(12) United States Patent
Komatsu et al.

(10) Patent No.: US 7,186,888 B2
(45) Date of Patent: Mar. 6, 2007

(54) COLD STRESS-RESPONSIVE CRTINTP GENE AND USE THEREOF

(75) Inventors: Setsuko Komatsu, Tsukuba (JP); Arun Sharma, Tsukuba (JP); Junji Hashimoto, Tsukuba (JP); Kengo Sakaguchi, Noda (JP)

(73) Assignees: National Institute of Agrobiological Sciences, Ibaraki (JP); Japan Science and Technology Agency, Saitama (JP)

( * ) Notice: Subject to any disclaimer, the term of this patent is extended or adjusted under 35 U.S.C. 154(b) by 312 days.

(21) Appl. No.: 10/304,454

(22) Filed: Nov. 25, 2002

(65) Prior Publication Data

US 2003/0200567 A1   Oct. 23, 2003

(30) Foreign Application Priority Data

Apr. 23, 2002   (JP) .............................. 2002-121275

(51) Int. Cl.
*C12N 15/82* (2006.01)
*C12N 15/09* (2006.01)
*C12N 15/29* (2006.01)
*A01H 5/00* (2006.01)
*A01H 5/10* (2006.01)

(52) U.S. Cl. ....................... 800/289; 800/278; 800/298; 800/295; 536/23.6; 435/320.1; 435/468; 435/430.1

(58) Field of Classification Search ................ 800/278, 800/298, 295, 320.2, 289; 536/23.6; 435/320.1, 435/468
See application file for complete search history.

(56) References Cited

U.S. PATENT DOCUMENTS 6,074,877 A * 6/2000 D'Halluin et al. .......... 435/468

OTHER PUBLICATIONS

Lazar et al. Molecular and Cellular Biology, Mar. 1988, vol. 8, No. 3, pp. 1247-1252.*
Broun et al. Science, Nov. 13, 1998, vol. 282, pp. 1315-1317.*
Sharma, A., et al., "Identification and Cloning of cDNA Encoding Proteins Showing Interaction with Rice Calreticulin," 24th Annual Meeting of the Molecular Biology Society of Japan, poster presentation (Nov. 26, 2001).
Li, Zhijun, et al., "Characterization of Calreticulin as a Phosphoprotein Interacting With Cold-Induced Protein Kinase in Rice," *Biol. Pharm. Bull.* 26(2):256-261 (2003).
Abbasi, Fida, et al., "OsCDPK13, a Calcium-dependent Protein Kinase Gene from Rice, Is Induced by Cold and Gibberellin in Rice Leaf Sheath," *Plant Mol. Biol.*, 55(4):541-552 (2004).
Medina, J., et al., "Developmental and Stress Regulation of RCI2A and RCI2B, Two Cold-Inducible Genes of Arabidopsis Encoding Highly Conserved Hydrophobic Proteins," *Plant Physiol*, 125(4): 1655-1666 (2001).
Saijo, Y., et al., "Over-expression of a single $Ca^{2+}$-dependent protein kinase confers both cold and salt/drought tolerance on rice plants," *The Plant Journal*, 23(3):319-327 (2000).
Corbett, E. F., et al., "$Ca^{2+}$ Regulation of Interactions Between Endoplasmic Reticulum Chaperones," J. Biol. Chem., 274:6203-6211 (1999).
Li, Z. and Komatsu, S., "Molecular Cloning and Characterization of Calreticulin, a Calcium-binding Protein Involed in the Regeneration of Rice Cultured Suspension Cells," *Eur. J. Biochem.*, 267:737-745 (2000).
Sharma, A., et al., "Identification and Cloning of cDNA Encoding Proteins Showing Interaction with Rice Calreticulin," 24th Annual Meeting of the Molecular Biology Society of Japan, p. 494 (Abstract No. 2P-079) (Nov. 26, 2001).
Sharma, A., et al., "Molecular Characterization of Calreticulin and its Interaction with a Novel Protein, CRTinP in Rice: Implications for their Potential Regulatory Role in Stress Response," *The FEBS Journal: 28th Meeting of the Federation of European Biochemical Societies*, 269:p. 6 (Abstract S1.6-5) (2002).

* cited by examiner

*Primary Examiner*—Medina A. Ibrahim
(74) *Attorney, Agent, or Firm*—Hamilton, Brook, Smith & Reynolds, P.C.

(57) ABSTRACT

The invention relates to isolated genes encoding polypeptides that interact with calreticulin (CRT), plants and plant cells transformed with the CRT genes for resistance against cold stress, and methods of producing the transformed plants and cells.

12 Claims, 4 Drawing Sheets

COLD STRESS-RESPONSIVE CRTINTP GENE AND USE THEREOF

RELATED APPLICATION

This application claims priority under 35 U.S.C. § 119 or 365 to Japanese Application No. 2002-121275, filed Apr. 23, 2002. The entire teachings of the above application are incorporated herein by reference.

BACKGROUND OF THE INVENTION

Growth disorders and reproductive disorders occur in plants outside their normal growth temperatures, which are different depending on the plants, and the plants are placed under extremely disadvantageous condition against species preservation (i.e., high stress condition). Therefore, plants have mechanisms to adapt to high and low temperature stresses by inducing the expressions of specific genes in response to these stresses (Naoki Sato, Tissue Culture, 19: 357 (1993); Thowashou M, Adv. Genet., 28: 99; (1990)). As to cold stress, in many cases, it takes a long time, such as several days, for plants to induce stress genes, as reported in the literature (Koga-ban Y, Abe M, and Kitagawa Y Plant Cell Physiol., 32: 901–905 (1991)).

Cytoplasmic calcium ions are recognized as second messengers for endogenous and environmental signaling in plants and animals. In plants, an increase in cytoplasmic calcium ions is caused by hormones such as auxin and abscisic acid, by non-biological environmental signals such as cold stress and mechanical stress, and by biological signals involved in recognition of commensals and pathogens.

In animals, calreticulin (CRT), which is a calcium binding protein, functions as a multi-functional regulatory factor involved in cell adhesion, maintenance of intracellular calcium homeostasis, protein folding, and environmental stress response (Kwor M S, Park C S, Choi K, Ahnn J, Kim J I, Eom S H, Kaujiman S J, and Song W K, Mol. Biol. Cell 11: 1433–1443 (2000)). It has already been confirmed that CRP55, Calregulin, HACBP, ERP60, CALBP, and CaBP3 are members of the CRT class. Rice CRT was cloned and is known to be involved in suppressing redifferentiation rate of rice callus and in regulating rice stem and leaf elongation (Li Z, Komatsu S, Eur. J. Biochem., 267: 737–745 (2002)). However, its molecular mechanism has not been well characterized.

SUMMARY OF THE INVENTION

This invention was performed in the light of such a situation. The objective of the present invention is to isolate and identify a gene encoding CRT-interacting polypeptide, and to provide the gene and its use. Specifically, the objective of the present invention is to provide the CRTintP gene, a transformed plant comprising this gene, and a method for producing the transformed plant.

The present inventors tried to isolate the gene encoding CRT-interacting polypeptide by the yeast two-hybrid method (Fields, Song, Nature, 340: 245–246 (1989)) since CRT is known to exhibit its function by interacting with other proteins (Corbett E F, Oikawa K, Francois P, Tessier O C, Kay C, Bergeron J J, Thomas D Y, Krause K H, and Michalak M, J. Biol. Chem., 274: 6203–6211(1999)). Specifically, the yeast two-hybrid method using a cDNA library derived from rice cultured cells was performed twice and the results of an experimental group were compared with those of a control group. As a result, a gene encoding CRT-interacting polypeptide (named CRTintP) was specifically detected. Furthermore, a full length cDNA encoding the CRTintP was isolated, and the gene was revealed to be a novel gene. In addition, analyses of the expressions of both CRT and CRTintP genes in rice leaf blade under cold stress revealed that the expressions were markedly induced 15 minutes after the application of cold stress and that the expressions reached a maximum at 30 min.

Thus, the present invention provides a polynucleotide selected from the group consisting of:
   (a) a polynucleotide encoding a polypeptide comprising the amino acid sequence of SEQ ID NO: 2;
   (b) a polynucleotide comprising a coding region of the nucleotide sequence of SEQ ID NO: 1;
   (c) a polynucleotide encoding a polypeptide comprising the amino acid sequence of SEQ ID NO: 2 in which one or more amino acids are substituted, deleted, added and/or inserted; and
   (d) a polynucleotide hybridizing under stringent conditions with a polynucleotide comprising the nucleotide sequence of SEQ ID NO: 1. Preferably, the polynucleotide is expressed in a plant in response to cold stress.

The present invention also provides a vector comprising the above polynucleotide.

Furthermore, the present invention relates to a transformed plant cell comprising the above polynucleotide in an expressible manner. The transformed plant cell may further comprise a polynucleotide encoding calreticulin.

The present invention also relates to a transformed plant comprising the above transformed plant cell and to a transformed plant that is a progeny or a clone of the above transformed plant.

Furthermore, the present invention features a propagation material of the above transformed plants.

Another feature of the present invention is a method of producing the above plant, the method comprising the steps of:

introducing into a plant cell
   (a) the above polynucleotide; or
   (b) the above polynucleotide and a polynucleotide encoding calreticulin; and regenerating the plant from the plant cell.

DETAILED DESCRIPTION OF THE INVENTION

The present invention provides a polynucleotide encoding the CRTintP. Preferably, the polynucleotide is expressed in response to cold stress in plants.

The polynucleotide of the present invention can be derived from any plant including, but not limited to, rice, soybeans, buckwheat, vegetables, root vegetables, fruit vegetable, and fruits.

In the present invention, cold stress can be induced in plants by transferring the plants from one temperature to a lower temperature. For example, cold stress can be induced in plants by transferring a rice plant or its segments at the seedling stage (2 weeks after germination) from room temperature to 5° C. for a period of time (2 minutes to 48 hours). However, the present invention is not limited to the method described above.

A polynucleotide encoding the CRTintP of the present invention includes, for example, a polynucleotide comprising the coding region of the nucleotide sequence of SEQ ID NO: 1 and a polynucleotide encoding a polypeptide comprising the amino acid sequence of SEQ ID NO: 2.

As used herein, an "isolated polynucleotide" is a polynucleotide the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in such a manner that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

Accordingly, in one aspect, the invention provides an isolated polynucleotide that encodes a polypeptide described herein or a fragment thereof. Preferably, the isolated polypeptide includes a nucleotide sequence that is at least 60% identical to the nucleotide sequence shown in SEQ ID NO: 1. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO: 1. In the case of an isolated polynucleotide which is longer than or equivalent in length to the reference sequence, e.g., SEQ ID NO: 1, the comparison is made with the full length of the reference sequence. Where the isolated polynucleotide is shorter than the reference sequence, e.g., shorter than SEQ ID NO: 1, the comparison is made to a segment of the reference sequence of the same length (excluding any loop required by the homology calculation).

The present invention includes a polynucleotide encoding a polypeptide that is structurally similar to the CRTintP of SEQ ID NO: 2 and that interacts with CRT (calreticulin). Preferably, the polynucleotide is expressed in response to cold stress in plants.

Whether or not a polynucleotide encodes CRT-interacting polypeptide can be determined by methods known to those skilled in the art. For example, these methods include yeast two-hybrid method, immunoprecipitation method, affinity column method, protein chip method, and sensor method.

In addition, whether or not a polynucleotide encodes a polypeptide expressed in response to cold stress can be determined by, for example, examining whether or not the polypeptide or an mRNA encoding the polypeptide is induced, depending on the cold stress, in plants transformed with the test polynucleotide.

Examples of such polynucleotides include those encoding mutants, derivatives, alleles, variants, and homologs that encode polypeptides comprising the amino acid sequence of SEQ ID NO: 2 in which one or more amino acids are substituted, deleted, added, and/or inserted.

An example of a method for preparing a polynucleotide encoding a polypeptide comprising altered amino acid sequence, which method is well known to those skilled in the art, includes site-directed mutagenesis (Kramer W and Fritz H-J, Methods Enzymol. 154: 350 (1987)). The amino acid sequence of a polypeptide may also be mutated in nature due to a mutation of the nucleotide sequence. A polynucleotide encoding polypeptides having the amino acid sequence of the wild-type CRTintP (SEQ ID NO: 2) in which one or more amino acids are substituted, deleted, added, and/or inserted are also included in the polynucleotide of the present invention, so long as it encodes a polypeptide functionally equivalent to the wild-type CRTintP. The number of amino acids that are mutated is not particularly restricted, as long as the polynucleotide of the present invention encodes a polypeptide functionally equivalent to the wild-type CRTintP (SEQ ID NO: 2). Normally, it is within 50 amino acids, preferably within 30 amino acids, more preferably within 10 amino acids, and even more preferably within 3 amino acids. The site of mutation may be any site, as long as the polynucleotide of the present invention encodes a polypeptide functionally equivalent to the wild-type CRTintP (SEQ ID NO: 2). Additionally, nucleotide sequence mutants that do not result in amino acid sequence changes in the polypeptide (degeneracy mutants) are also included in the polynucleotide of the present invention.

An amino acid substitution is preferably mutated into different amino acid(s) in which the properties of the amino acid side-chain are conserved. A "conservative amino acid substitution," as employed in the present invention, refers to a replacement of one amino acid residue belonging to one of the following groups with similar side chain(s) with another amino acid from the same group. Groups of amino acid residues having similar side chains are well known to one of ordinary skill in the art. These groups include the following: amino acids with basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine); nonpolar side chains (e.g., alanine, valine, leucine, isoleucine, proline, phenylalanine, methionine, tryptophan); beta-branched side chains (e.g., threonine, valine, isoleucine); and aromatic side chains (e.g., tyrosine, phenylalanine, tryptophan, histidine).

A polynucleotide encoding a polypeptide functionally equivalent to the CRTintP described in SEQ ID NO: 2 can be prepared using methods well known to those skilled in the art, such as hybridization techniques (Southern E M, J. Mol. Biol., 98: 503 (1975)) and the polymerase chain reaction (PCR) technique (Saiki R K, et al., Science, 230: 1350 (1985); Saiki R K, et al., Science, 239: 487 (1988)). That is, it is routine for a person skilled in the art to isolate polynucleotide with high homology to the CRTintP gene from rice and other plants using the CRTintP gene (SEQ ID NO: 1) or parts thereof as a probe, and oligonucleotides hybridizing specifically to the CRTintP gene (SEQ ID NO:

1) as a primer. Such polynucleotides encoding polypeptides functionally equivalent to the CRTintP, which are obtainable by hybridization techniques or PCR techniques, are included in the polynucleotide of this invention.

Hybridization reactions to isolate such polynucleotides are preferably conducted under stringent conditions. Stringent hybridization conditions of the present invention include conditions such as: 6 M urea, 0.4% sodium dodecyl sulfate (SDS), and 0.5×SSC; and those comprising a stringency equivalent to that of the conditions. Polynucleotides with higher homology are expected to be isolated efficiently when hybridization is performed under higher stringency conditions, for example, 6 M urea, 0.4% SDS, and 0.1×SSC. Herein, "high homology" means an identity of at least 50% or more, more preferably 70% or more, even more preferably 90% or more, and most preferably 95% or more, in the whole amino acid sequence.

The degree of identity of one amino acid sequence or nucleotide sequence to another can be determined by following the BLAST algorithm by Karlin and Altschul (Karlin S and Altschul S F, Proc. Nati. Acad. Sci. USA, 87: 2264–2268 (1990); and Karlin S and Altschul SF, Proc. Nati. Acad. Sci, USA, 90: 5873–5877 (1993)). Programs called BLASTN and BLASTX were developed based on the BLAST algorithm (Altschul S F, et. al., J. Mol. Biol. 215: 403 (1990)). To analyze a nucleotide sequence according to BLASTN, parameters are set, for example, at score=100 and word length=12. On the other hand, parameters used for the analysis of amino acid sequences according to BLASTX include, for example, score=50 and word length=3. When BLAST and Gapped BLAST programs are used, default parameters of each program are used. Specific techniques for such analysis are known, see, for example, the website for the National Center for Biotechnology Information.

A polynucleotide encoding the CRTintP of the present invention includes a genomic DNA, a cDNA, and a chemically synthesized DNA. There is no restriction on length of the polynucleotide of the present invention, but it preferably comprises at least 15 nucleotides. A genomic DNA and cDNA can be prepared according to conventional methods known to those skilled in the art. More specifically, the CRTintP genomic DNA can be prepared, for example, as follows: (1) extracting genomic DNA from rice cultivars comprising the CRTintP gene; (2) constructing a genomic library (utilizing a vector, such as a plasmid, phage, cosmid, BAC, PAC); (3) spreading the genomic library; and (4) conducting colony hybridization or plaque hybridization using a probe prepared based on the polynucleotide of the present invention (e.g. SEQ ID NO: 1). Alternatively, the CRTintP genomic DNA can be prepared by PCR, using primers specific to a polynucleotide of the present invention (e.g., SEQ ID NO: 1). On the other hand, the CRTintP cDNA can be prepared, for example, as follows: (1) synthesizing cDNAs based on MRNA extracted from rice cultivars comprising the CRTintP gene; (2) preparing a cDNA library by inserting the synthesized cDNA into vectors, such as λZAP; (3) spreading the cDNA library; and (4) conducting colony hybridization or plaque hybridization as described above. Alternatively, the CRTintP cDNA can be also prepared by PCR.

Moreover, a polynucleotide encoding the CRTintP was isolated as a polynucleotide encoding the CRT-interacting polypeptide. On the other hand, it is known that the use of a polynucleotide encoding CRT enables adding dwarf character and cold stress-responsive character to plants. Therefore, a polynucleotide of the present invention can be a tool to isolate such useful polynucleotides.

Moreover, the CRTintP interacts with CRT, which is involved in suppressing redifferentiation rate of rice callus and also is involved in regulating stem and leaf elongation in rice. Therefore, it is possible that the CRTintP also regulates redifferentiation rate of plant cell, as well as stem and leaf elongation. Thus, the polynucleotide of the present invention can be used to produce plant cells that have modified redifferentiation rate and transformed plants that have modified stem and leaf elongation.

The present invention revealed that both the polynucleotide encoding the CRTintP and the polynucleotide encoding CRT respond to cold stress. Therefore, both the polynucleotides can be used to produce transformed plants that are resistant to low temperature.

A method of producing transformed plants in the present invention comprises the following steps: (a) introducing, into a plant cell, a vector into which the polynucleotide of the present invention or a polynucleotide encoding CRT and the polynucleotide of the present invention are inserted, and (b) regenerating a plant from the transformed plant cell.

Plant cells from any type of plant can be used for the present invention. Moreover, there is no limitation on vectors used for the transformation of plant cells so long as the vectors can express the inserted genes in the plant cells. For example, vectors comprising a promoter for constitutive gene expression in plant cells (e.g., the cauliflower mosaic virus 35S promoter) and a promoter inducibly activated by exogenous stimuli can be used. The term "plant cell" as used in this invention includes various forms of plant cells, such as suspension culture cells, protoplasts, leaf sections and callus.

A vector can be introduced into plant cells using methods known to one skilled in the art, such as, the polyethylene glycol method, electroporation, *Agrobacterium*-mediated transfer, and particle bombardment. In *Agrobacterium*-mediated transfer, for example, the ultra high-speed transformation of monocotyledons (Japanese Patent No. 3141084) can be used. In particle bombardment, for example, the instrument from Bio-Rad Laboratory can be used. Plants can be regenerated from transformed plant cells by known methods according to the type of plant cell (Toki S, et al., Plant Physiol., 100: 1503 (1995)).

For example, several methods of transformation and regeneration in rice plants have been established and widely used in the art, the methods comprise the following: (1) the method of introducing genes into protoplasts using polyethylene glycol and regenerating the plant from them (suitable for Indica rice cultivars) (Datta S K, In "Gene Transfer To Plants", Potrykus I and Spangenberg, Eds, pp. 66–74 (1995)); (2) the method of introducing genes into protoplasts using an electric pulse and regenerating the plant from them (suitable for Japonica rice cultivars) (Toki S, et al., Plant Physiol., 100, 1503 (1992)); (3) the method of introducing genes directly into cells by particle bombardment and regenerating the plant from them (Christou P, et al., Biotechnology 9: 957 (1991)); and (4) the method of introducing genes using *Agrobacterium* into cells and regenerating the plant from them (Hiei Y, et al., Plant J., 6: 271 (1994)). Such methods can be suitably used in the present invention. Tobacco BY-2 cells, for example, are suitable for particle bombardment to introduce genes. Tobacco BY-2 cells can be easily obtained from facilities such as a cell bank.

Once a transformed plant is obtained in which the polynucleotide of the present invention is introduced into the genome, it is possible to gain progenies from that plant by sexual or asexual propagation. Alternatively, plants can be mass-produced from propagation materials (for example, seeds, fruits, grafts, tubers, tuberous roots, roots, callus, protoplasts) obtained from the plant, as well as progeny or clone thereof. The present invention includes a transformed plant cell into which the polynucleotide of the present invention or both the polynucleotide of the present invention and the polynucleotide encoding CRT have been introduced; a plant comprising the cell, a progeny and clone thereof, as well as a propagation material of the plant, progeny and clone thereof.

It is conceivable that the thus-produced plants are resistant to low temperature compared with wild-type plants. The present invention is very useful for growing agricultural products, preferably useful agricultural crops, in cold climates. Moreover, the transformed plant of the present invention can be used to produce the polypeptide encoded by the polynucleotide of the present invention. The polypeptide thus produced is useful for isolating CRT and the polynucleotide encoding CRT, which are involved in cold stress response and dwarfism. Thus, the present invention also relates to a polypeptide encoded by the polynucleotide of the present invention; and a method for producing the polypeptide, the method comprising use of the transformed plant of the present invention.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example by column chromatography, polyacrylamide gel electrophoresis, or HPLC analysis.

The present inventors have provided the polynucleotide encoding the CRTintP. The polynucleotide can be used not only for isolating polynucleotide encoding CRT but also for developing breeding material which is resistant to cold stress.

Any patents, patent applications and publications cited herein are incorporated in full by reference.

Herein, "%" for concentration denotes weight per volume percent, unless otherwise specified.

The present invention is illustrated via examples below; however it is not to be construed as being limited thereto.

EXAMPLE 1

CRT is involved in suppression of redifferentiation rate of rice callus and in the regulation of stem and leaf elongation in rice plant. However, the molecular mechanisms of the actions have not been well understood. To understand the mechanisms, CRT-interacting genes were isolated (Table 1) using the yeast two-hybrid method (Fields, Song, Nature, 340: 245–246 (1989)). Specifically, the yeast two-hybrid method using a cDNA library derived from rice culture cell was conducted twice, and the results of an experiment group were compared with those of a control group. As a result, the number of CRT-interacting clones was 6 in experiment 1 and 15 in experiment 2. Genetic analysis for these 21 clones revealed that the clones were derived from the same mRNA. The present inventors named the CRT-interacting protein as CRTintP. Further, RuBisCO activase, which was not expressed in culture cells, was used as a control for two-hybrid method. The results showed that RuBisCO activase did not bind to the CRTintP. The number of other clones which interacted with CRT was zero in experiment 1 and six in experiment 2. These six clones did not encode the CRTintP and were considered to be derived from RNA different from one another, but the function of the clones was unknown.

TABLE 1

|  | Control (RuBisCO activase) | CRT #1 | CRT #2 |
|---|---|---|---|
| CRTintP | 0 | 6 | 15 |
| Others | 23 | 1 | 6 |
| Total | 23 | 7 | 21 |

EXAMPLE 2

A full length CRTintP cDNA was isolated by screening a cDNA library (rice leaf blade derived) with partial nucleotide sequences of the CRT-interacting genes that had been redundantly detected compared with the control in the two experiment groups. As a result, the present inventors revealed that the CRTintP gene contained 3401 base pairs and encoded 966 amino acids (SEQ ID NO: 1). Moreover, the gene isolated by the present inventors was not registered in the database such as DDBJ and was identified as a novel gene. The present inventors also revealed that the gene encoded a protein with a molecular weight of approximately 100,000 daltons.

EXAMPLE 3

Figure 1:
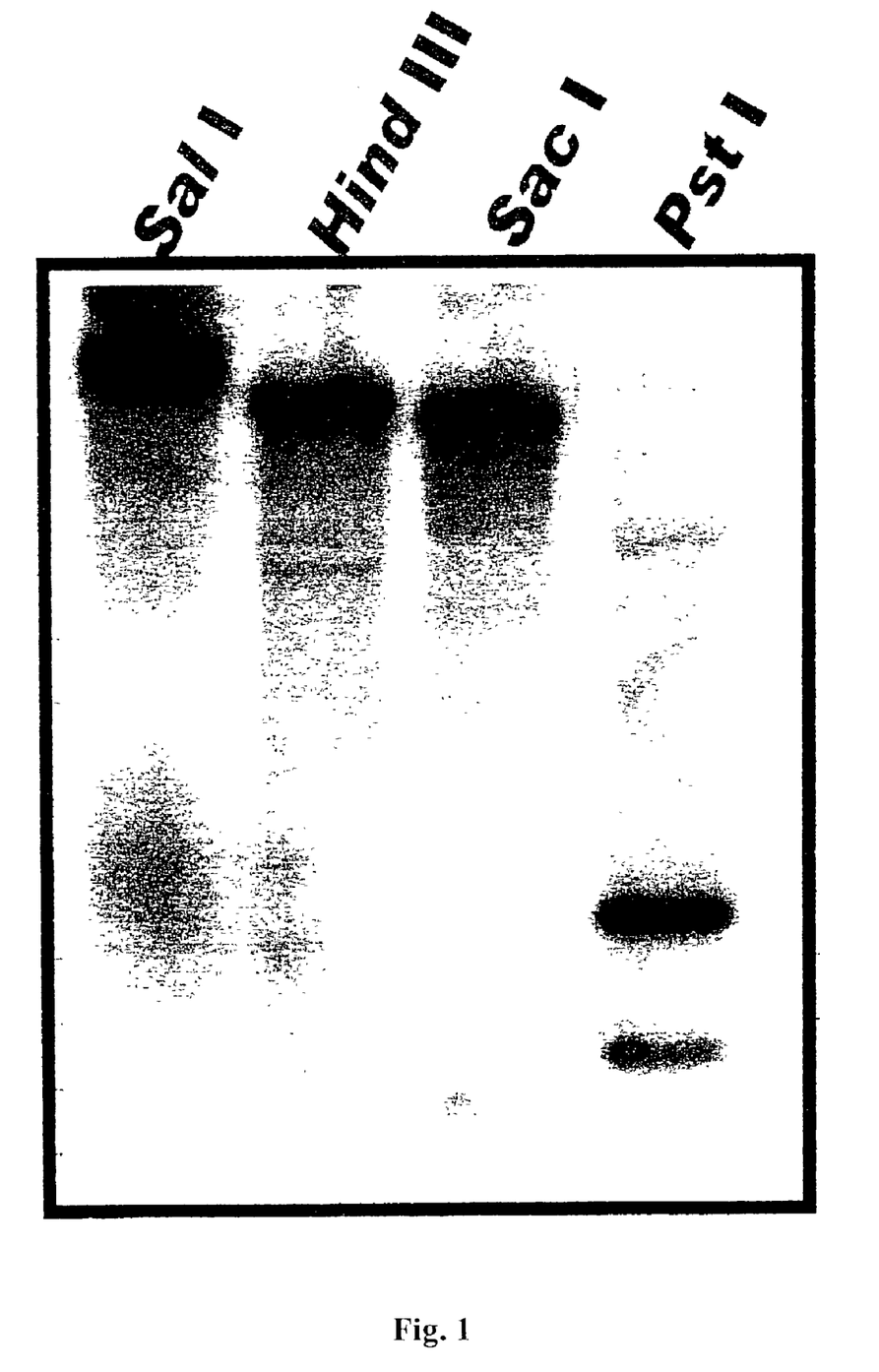
FIG. 1 is a photograph that shows a Southern blot of CRTintP gene.

Southern hybridization was performed to determine the copy number of CRTintP gene in the genome. An [$\alpha$-$^{32}$P] dCTP labeled 2300 base pair DNA probe which was derived from the CRTintP cDNA was used. Hybridization was done at 42° C. The result showed that there was one copy of the CRTintP gene in the rice genome (FIG. 1).

EXAMPLE 4

Figure 2:
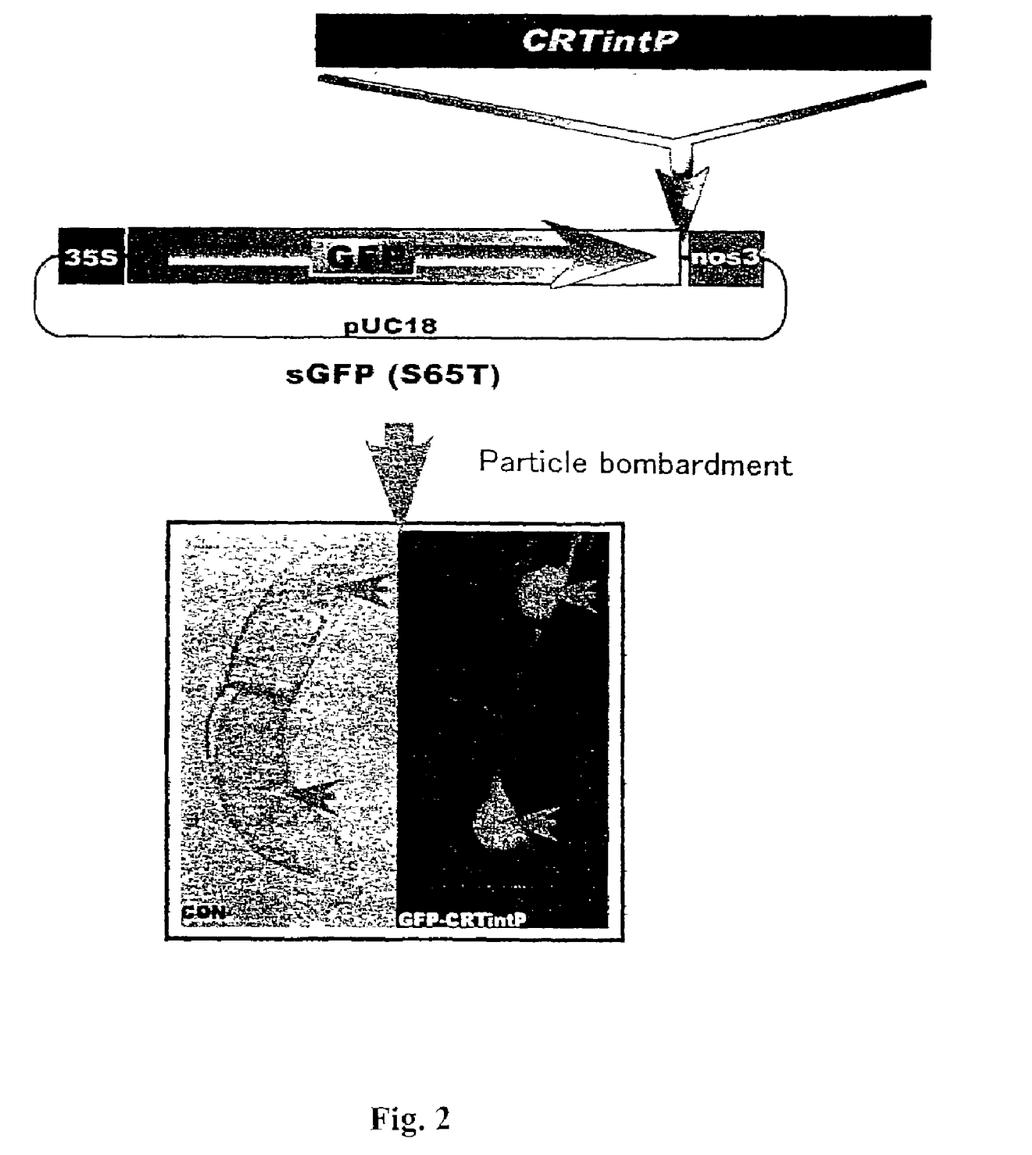
FIG. 2 is a schematic illustration that shows the structure of a vector carrying GFP-fused CRTintP and a photograph that shows the intracellular localization of GFP-fused CRTintP. "sGFP (S65T)" in the illustration indicates the name of the vector, and "CON" in the photograph indicates a control.

A GFP-fused CRTintP gene was introduced into tobacco BY-2 cells using the particle bombardment method in order to determine the intracellular localization of GFP-fused CRTintP. Specifically, 5 μg of DNA (a construct which expresses GFP-fused CRTintP under the control of the cauliflower mosaic virus 35S promoter) was coated on 3 mg of gold particles. These particles were bombarded at 1100 psi. The cells into which the GFP-CRTintP gene was introduced showed green fluorescence, but control cells did not show green fluorescence. Green fluorescence was localized in the nucleus of the cell as shown in FIG. 2. Thus, it was revealed that CRTintP was localized in the cell nucleus.

EXAMPLE 5

Figure 3:
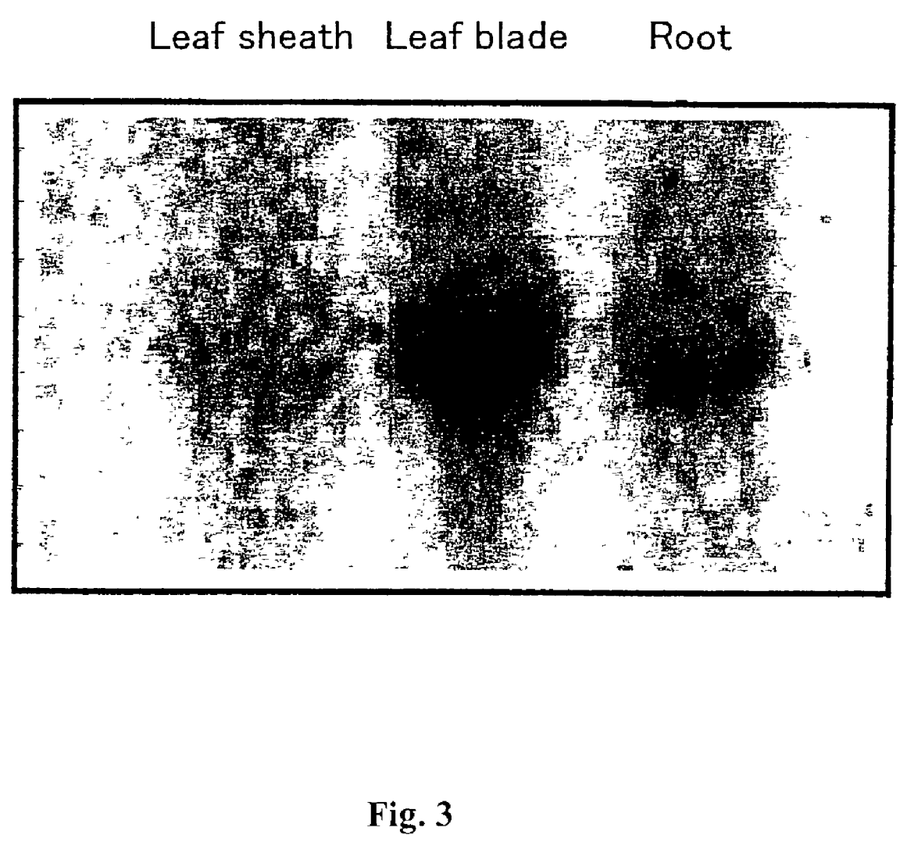
FIG. 3 is a photograph that shows the tissue specificity of CRTintP gene.

Northern blot analysis was conducted in order to determine the tissue specificity of CRTintP. First, RNAs were extracted from leaf sheath, leaf blade, and root. Then, they were subjected to electrophoresis on 1.2% denaturing agarose gel. Hybridization with $^{32}$P-labeled DNA (2300 bp) derived from the CRTintP cDNA as a probe was conducted using ULTRA hyb at 42° C. overnight. The results obtained demonstrated that the CRTintP gene was mainly expressed in the leaf blade (FIG. 3).

EXAMPLE 6

Figure 4:
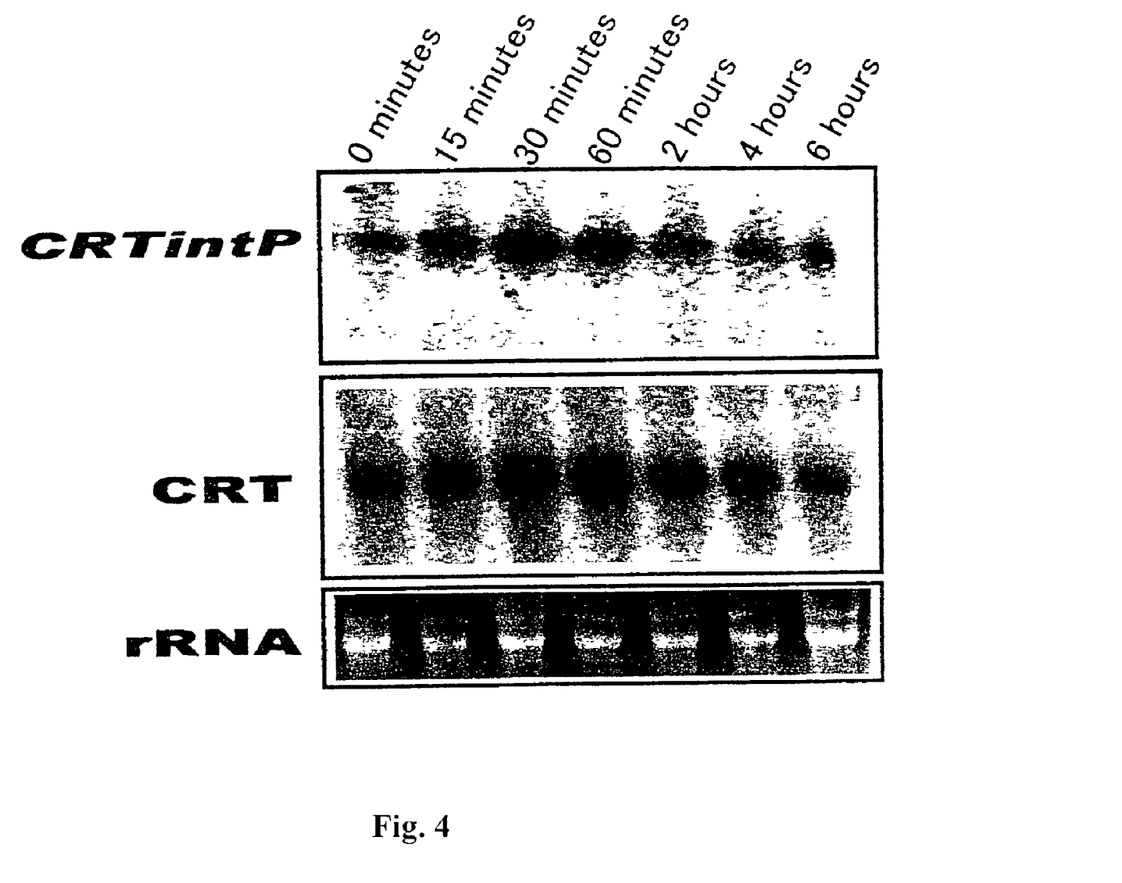
FIG. 4 is a photograph that shows the response of CRT and CRTintP genes to cold stress.

Northern blot analysis was conducted to examine the response of CRT and CRTintP against cold stress. First, rice (Nipponbare) was transferred to low temperature (from 25° C. to 5° C. with 75% humidity) and then samples were collected in triplicate at random from 20 plants every one hour. Northern blot analysis showed that both CRT and CRTintP expression started to increase markedly 15 min. after the start of cold stress and reached a maximum at 30 min. Thereafter, the expression of CRT and CRTintP began to decline (FIG. 4).

Thus, it was revealed that the expression of CRTintP, as well as CRT, was markedly increased about 30 min. after the start of cold stress. It is predicted that introduction of these genes into a plant and overexpression of the genes in the plant endows cold stress resistance to the transformed plants.

What is claimed is:

1. An isolated polynucleotide selected from the group consisting of:
   (a) a polynucleotide encoding a polypeptide comprising the amino acid sequence of SEQ ID NO: 2;
   (b) a polynucleotide comprising a nucleotide sequence of positions 296–3196 of the nucleotide sequence of SEQ ID NO: 1;
   (c) a polynucleotide encoding a polypeptide comprising an amino acid sequence that is at least about 95% identical to the amino acid sequence of SEQ ID NO: 2, wherein expression of the of the polynucleotide is increased in response to cold-stress of a plant, and wherein the polypeptide interacts with calreticulin; and
   (d) a polynucleotide hybridizing under stringent conditions of 6 M urea, 0.4% SDS and 0.1×SSC with the complement of SEQ ID NO: 1, wherein expression of the polynucleotide is increased in response to cold-stress of a plant and the polynucleotide encodes a polypeptide that is at least about 95% identical to the amino acid sequence of SEQ ID NO: 2, and said polypeptide interacts with calreticulin.

2. The isolated polynucleotide according to claim 1, wherein the polynucleotide is expressed in a plant in response to cold stress.

3. A vector comprising the isolated polynucleotide according to claim 1.

4. A transformed plant cell comprising the isolated polynucleotide according to claim 1.

5. The transformed plant cell according to claim 4, further comprising a polynucleotide encoding caireticulin.

6. A transformed plant comprising the transformed plant cell according to claim 4.

7. A transformed plant comprising the transformed plant cell according to claim 5.

8. A transformed plant that is a progeny of the transformed plant according to claim 6.

9. A transformed plant that is a progeny of the transformed plant according to claim 7.

10. A propagation material of the transformed plant according to claim 6, wherein the propagation material contains the isolated polynucleotide.

11. A propagation material of the transformed plant according to claim 7, wherein the propagation material contains the isolated polynucleotide.

12. A method of producing a plant, the method comprising the steps of: introducing into a plant cell
   (a) the isolated polynucleotide according to claim 1; or
   (b) the isolated polynucleotide according to claim 1 and a polynucleotide encoding rice calreticulin; and
   regenerating the plant from the plant cell.

\* \* \* \* \*

UNITED STATES PATENT AND TRADEMARK OFFICE
CERTIFICATE OF CORRECTION

| | | |
|---|---|---|
| PATENT NO. | : 7,186,888 B2 | Page 1 of 1 |
| APPLICATION NO. | : 10/304454 | |
| DATED | : March 6, 2007 | |
| INVENTOR(S) | : Setsuko Komatsu et al. | |

It is certified that error appears in the above-identified patent and that said Letters Patent is hereby corrected as shown below:

In Column 21, line 21:

Claim 1, line 11, after the word "expression" and before the word "polynucleotide", delete the second occurrence of the words "of the"; and In Column 22, line 13:

Claim 5, line 2, last word, delete "caireticulin" and insert therefor --calreticulin--.

Signed and Sealed this

Seventh Day of August, 2007

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 3401
<212> TYPE: DNA
<213> ORGANISM: Oryza sativa
<220> FEATURE:
<221> NAME/KEY: CDS
<222> LOCATION: (296)...(3196)

<400> SEQUENCE: 1
gagttctcac ttctcacaca actcgcaacc ctaataaagc gcaaaaaagg aaaaagaaaa      60
atcgccacgg aaaaatcctc gctgccccc atcgggcagg agcaaccgcc gcatcggccc     120
ccgatccggt cgccgccgcc tctcgcccgg ttcatccgcc gcttgccaac ccctccgctc     180
ccagcaaccc tagtccccca ccccaacgcc gccgccagct cagctcgcct cgcgcggggc     240
gcagccgact ctctacttgt ggcctcggcg gctcgggccc tctccggatt ccacg atg     298
                                                                  Met
                                                                    1 tct gaa gat gcg tct gtc ggg gcc agc agt tca aca gta aaa gct ggc     346
Ser Glu Asp Ala Ser Val Gly Ala Ser Ser Ser Thr Val Lys Ala Gly
          5                  10                  15 gat gat cca gag gct acc att gag atc aac atc aaa acc ctg gat tca     394
Asp Asp Pro Glu Ala Thr Ile Glu Ile Asn Ile Lys Thr Leu Asp Ser
     20                  25                  30 caa gtt cat aag ctc cgt gtt aag aag aat gta cct gtt ctg gtc ctt     442
Gln Val His Lys Leu Arg Val Lys Lys Asn Val Pro Val Leu Val Leu
 35                  40                  45 aaa gag aag ata gta gag gca acc ggg gtt cct gtg gac caa cag cgg     490
Lys Glu Lys Ile Val Glu Ala Thr Gly Val Pro Val Asp Gln Gln Arg
 50                  55                  60                  65 ttg att ttt aga gga aga gtc tta aag gac gat cac ctg cta tca gaa     538
Leu Ile Phe Arg Gly Arg Val Leu Lys Asp Asp His Leu Leu Ser Glu
                 70                  75                  80 tat cat ttg gaa gat ggg tac aca ttg cat ttg gtt gct cgg cgt gca     586
Tyr His Leu Glu Asp Gly Tyr Thr Leu His Leu Val Ala Arg Arg Ala
             85                  90                  95 gct gct gaa ggc caa cat tct tct ggt act tct gat gaa aac acc cat     634
Ala Ala Glu Gly Gln His Ser Ser Gly Thr Ser Asp Glu Asn Thr His
            100                 105                 110 gct aat gtt aat gtt gct gga aat gga ctg tta gga gat atc tcc agg     682
Ala Asn Val Asn Val Ala Gly Asn Gly Leu Leu Gly Asp Ile Ser Arg
        115                 120                 125 agt gtt cgg gat atc ctt ggc tcc cta ggt ctt gcg acg cct ggt ggc     730
Ser Val Arg Asp Ile Leu Gly Ser Leu Gly Leu Ala Thr Pro Gly Gly
130                 135                 140                 145 atg aca aac act aca ttt tcg gtg cct tta acc act gca cca aaa ggg     778
Met Thr Asn Thr Thr Phe Ser Val Pro Leu Thr Thr Ala Pro Lys Gly
                150                 155                 160
```

-continued

| | |
|---|---|
| gcc aat aat gtc aat gga aga act caa cca ggg aat cat gca caa cca<br>Ala Asn Asn Val Asn Gly Arg Thr Gln Pro Gly Asn His Ala Gln Pro<br>                165                    170                 175 | 826 |
| ggg ttt tca att ctg aat cat caa atc caa gta tca caa cta caa cca<br>Gly Phe Ser Ile Leu Asn His Gln Ile Gln Val Ser Gln Leu Gln Pro<br>       180                    185                    190 | 874 |
| gca ggc tct att cct cgc aac atg gtt att cct gat tct ctc aca act<br>Ala Gly Ser Ile Pro Arg Asn Met Val Ile Pro Asp Ser Leu Thr Thr<br>195                    200                    205 | 922 |
| ctt ttg gag tat atc aac cgc atg gat caa gta cta cag aat aac ggc<br>Leu Leu Glu Tyr Ile Asn Arg Met Asp Gln Val Leu Gln Asn Asn Gly<br>210                    215                    220                 225 | 970 |
| aca cca tct gtt gat aca aat acc cag cag cca cca aga tcg gat gat<br>Thr Pro Ser Val Asp Thr Asn Thr Gln Gln Pro Pro Arg Ser Asp Asp<br>                230                    235                 240 | 1018 |
| gct tat cta aat caa aga ttt cca agt cct gag gtt ctg gtg tca gtc<br>Ala Tyr Leu Asn Gln Arg Phe Pro Ser Pro Glu Val Leu Val Ser Val<br>                    245                    250                    255 | 1066 |
| att gaa aga gcc caa caa ctt ctt ggt ggc agt gct gct tct gct ctt<br>Ile Glu Arg Ala Gln Gln Leu Leu Gly Gly Ser Ala Ala Ser Ala Leu<br>260                    265                    270 | 1114 |
| tca cat ctc gca caa cca atc cag aga gat tct ggc acc agt gat gca<br>Ser His Leu Ala Gln Pro Ile Gln Arg Asp Ser Gly Thr Ser Asp Ala<br>                275                    280                 285 | 1162 |
| tct ata cgt agc cag atc cag aat gaa tca gct cag ctg gga gta gca<br>Ser Ile Arg Ser Gln Ile Gln Asn Glu Ser Ala Gln Leu Gly Val Ala<br>290                    295                    300                 305 | 1210 |
| atg cag cat ttg ggt gca atg ttt ttg gag ctt ggt cga aca atg atg<br>Met Gln His Leu Gly Ala Met Phe Leu Glu Leu Gly Arg Thr Met Met<br>                    310                    315                 320 | 1258 |
| atg ctt cgg atg ggg cca tcc cct gct gat gct ttt gtc aat gct gga<br>Met Leu Arg Met Gly Pro Ser Pro Ala Asp Ala Phe Val Asn Ala Gly<br>                325                    330                 335 | 1306 |
| tct tct gtt tat ata aac tct gca gga ccg aat cca atc atg gtt cag<br>Ser Ser Val Tyr Ile Asn Ser Ala Gly Pro Asn Pro Ile Met Val Gln<br>                    340                    345                 350 | 1354 |
| cca tct ttt caa aat act cct cct ttt gga gtt tcg agc ata cca gtc<br>Pro Ser Phe Gln Asn Thr Pro Pro Phe Gly Val Ser Ser Ile Pro Val<br>355                    360                    365 | 1402 |
| ctc ggt gga att tct ggt gcc ttt ggt att gtt gat cct tct cgt aca<br>Leu Gly Gly Ile Ser Gly Ala Phe Gly Ile Val Asp Pro Ser Arg Thr<br>370                    375                    380                 385 | 1450 |
| tct gct gtc aat acc cat ggt act tct aca aca agt ggg tca tct gct<br>Ser Ala Val Asn Thr His Gly Thr Ser Thr Thr Ser Gly Ser Ser Ala<br>                390                    395                 400 | 1498 |
| ggt atg acc act gct tct gca ggc gct gtc aat gaa ggt cgt caa aat<br>Gly Met Thr Thr Ala Ser Ala Gly Ala Val Asn Glu Gly Arg Gln Asn<br>                    405                    410                 415 | 1546 |
| gtg gaa aga act caa gga ggt aac cca tct gct acc tca atg cat gga<br>Val Glu Arg Thr Gln Gly Gly Asn Pro Ser Ala Thr Ser Met His Gly<br>                    420                    425                 430 | 1594 |
| ttg cca gca agg aca gtt att gcg gct att cct gca cgg tcc acg gct<br>Leu Pro Ala Arg Thr Val Ile Ala Ala Ile Pro Ala Arg Ser Thr Ala<br>435                    440                    445 | 1642 |
| gag gct cca aac cat gtc ctg agt gtt atc ctg cct gtt caa gtg agg<br>Glu Ala Pro Asn His Val Leu Ser Val Ile Leu Pro Val Gln Val Arg<br>450                    455                    460                 465 | 1690 |
| agt caa gta gca atg cct aat caa tca aca gtt tct caa ggt tct cag<br>Ser Gln Val Ala Met Pro Asn Gln Ser Thr Val Ser Gln Gly Ser Gln<br>                470                    475                 480 | 1738 |

-continued

| | | |
|---|---|---|
| act gca gtg ggc ggt gga tct caa cca caa gcc tct gta ggt ggt gtt<br>Thr Ala Val Gly Gly Gly Ser Gln Pro Gln Ala Ser Val Gly Gly Val<br>          485                    490                   495 | | 1786 |
| gct agc att cct tct ata gtg gca cag gta act gca caa gta gcc aat<br>Ala Ser Ile Pro Ser Ile Val Ala Gln Val Thr Ala Gln Val Ala Asn<br>          500                    505                   510 | | 1834 |
| gca ttg agt gca aat caa caa ggc cag gtt tca tca tct gcg cag aac<br>Ala Leu Ser Ala Asn Gln Gln Gly Gln Val Ser Ser Ser Ala Gln Asn<br>          515                    520                   525 | | 1882 |
| aca gta gat cag gga tct cgc tcg gtc aca act aat gga gtt gac aat<br>Thr Val Asp Gln Gly Ser Arg Ser Val Thr Thr Asn Gly Val Asp Asn<br>530                   535                   540                   545 | | 1930 |
| gtg gat tct ctg gta tca gca agt acg caa ctg caa aat gag ctg tca<br>Val Asp Ser Leu Val Ser Ala Ser Thr Gln Leu Gln Asn Glu Leu Ser<br>          550                    555                   560 | | 1978 |
| gat tct aac aat gga cgc act tca cta aat gca caa tct ctt gta gct<br>Asp Ser Asn Asn Gly Arg Thr Ser Leu Asn Ala Gln Ser Leu Val Ala<br>          565                    570                   575 | | 2026 |
| gga gca ggt att tct cct tca aac aca tct gat ccc aat tta gca tcg<br>Gly Ala Gly Ile Ser Pro Ser Asn Thr Ser Asp Pro Asn Leu Ala Ser<br>                580                   585                   590 | | 2074 |
| gaa gac agc agc act gaa aat gct ccc aac atc ggc agt att caa caa<br>Glu Asp Ser Ser Thr Glu Asn Ala Pro Asn Ile Gly Ser Ile Gln Gln<br>595                   600                   605 | | 2122 |
| cat cca gag atg gaa ggg atc cat gca gat aat gtc aga aaa cct tct<br>His Pro Glu Met Glu Gly Ile His Ala Asp Asn Val Arg Lys Pro Ser<br>610                   615                   620                   625 | | 2170 |
| gag gaa tca aca aca gcc aac tta gtg ggg cag atc aca acc acc tgt<br>Glu Glu Ser Thr Thr Ala Asn Leu Val Gly Gln Ile Thr Thr Thr Cys<br>                630                   635                   640 | | 2218 |
| aca gat gat att tct gtg aac aga tca gca gaa aat tct tca cag aag<br>Thr Asp Asp Ile Ser Val Asn Arg Ser Ala Glu Asn Ser Ser Gln Lys<br>                645                   650                   655 | | 2266 |
| aac att cca ttg gat gga gta tct gca cag tcc att aag cca tct gca<br>Asn Ile Pro Leu Asp Gly Val Ser Ala Gln Ser Ile Lys Pro Ser Ala<br>          660                    665                   670 | | 2314 |
| agt agt agg tct gaa cca gta ggt ctt ggt gga ggt ttg cag cct aag<br>Ser Ser Arg Ser Glu Pro Val Gly Leu Gly Gly Gly Leu Gln Pro Lys<br>675                   680                   685 | | 2362 |
| agg cgg agc aga aca gca aag cca cct ggg agt agc agt gat act ggc<br>Arg Arg Ser Arg Thr Ala Lys Pro Pro Gly Ser Ser Ser Asp Thr Gly<br>690                   695                   700                   705 | | 2410 |
| gaa gtc gtc aat tcc tct cgc atc agc aat agc caa aat gct gtt tca<br>Glu Val Val Asn Ser Ser Arg Ile Ser Asn Ser Gln Asn Ala Val Ser<br>                710                   715                   720 | | 2458 |
| atg ggc cag cag gtt ctg caa gcc ctt gct tct caa aat act aat gta<br>Met Gly Gln Gln Val Leu Gln Ala Leu Ala Ser Gln Asn Thr Asn Val<br>          725                    730                   735 | | 2506 |
| aac aga agc cat gtt acg gat tct cca ctt cca tcc act act tct cag<br>Asn Arg Ser His Val Thr Asp Ser Pro Leu Pro Ser Thr Thr Ser Gln<br>          740                    745                   750 | | 2554 |
| ttt tct ggt gga atg cct ccg aga aga cag ggt ggt gaa gga caa gtt<br>Phe Ser Gly Gly Met Pro Pro Arg Arg Gln Gly Gly Glu Gly Gln Val<br>755                     760                   765 | | 2602 |
| gat ttt ggc agt atg ata tcc agt gtg cta aac aac cca gct ttt ggc<br>Asp Phe Gly Ser Met Ile Ser Ser Val Leu Asn Asn Pro Ala Phe Gly<br>770                   775                   780                   785 | | 2650 |
| aat ctg ttg tcc aat gta gca gag caa aca ggc atg ggt tcc gca ggt<br>Asn Leu Leu Ser Asn Val Ala Glu Gln Thr Gly Met Gly Ser Ala Gly | | 2698 |

-continued

```
             790                 795                 800
gat ttg aga aac atg gtg gaa gag tgt gca cag agc cct gca ata atg    2746
Asp Leu Arg Asn Met Val Glu Glu Cys Ala Gln Ser Pro Ala Ile Met
            805                 810                 815 gat act atg agt aat tta gtc caa aat gtg gat ggg tca gga aga ggt    2794
Asp Thr Met Ser Asn Leu Val Gln Asn Val Asp Gly Ser Gly Arg Gly
            820                 825                 830 caa ggt ggc att gac ttg tct aga atg atg cag caa atg atg cct gtt    2842
Gln Gly Gly Ile Asp Leu Ser Arg Met Met Gln Gln Met Met Pro Val
        835                 840                 845 gta tcc caa gtt ctt ggt gga gct ggg gct cgt cct gct ggt aca aat    2890
Val Ser Gln Val Leu Gly Gly Ala Gly Ala Arg Pro Ala Gly Thr Asn
850                 855                 860                 865 agt gga caa tcc aga ttg cag cct cgg cgc agt gac atg aga gtg gat    2938
Ser Gly Gln Ser Arg Leu Gln Pro Arg Arg Ser Asp Met Arg Val Asp
                870                 875                 880 gat gct tca gat tat gga aat tct cag att gat cta cac caa gct cgt    2986
Asp Ala Ser Asp Tyr Gly Asn Ser Gln Ile Asp Leu His Gln Ala Arg
            885                 890                 895 gaa cac att gag caa cat gac tcc ccc agg gat atc ttc ggt gcg gtc    3034
Glu His Ile Glu Gln His Asp Ser Pro Arg Asp Ile Phe Gly Ala Val
        900                 905                 910 ctc gaa act gct gca cag gct tat ggt gaa gat gag agt att gag gac    3082
Leu Glu Thr Ala Ala Gln Ala Tyr Gly Glu Asp Glu Ser Ile Glu Asp
    915                 920                 925 atg ctt gaa gag ctt gtc agt gac cca gaa ctt aca gat gac tac ctg    3130
Met Leu Glu Glu Leu Val Ser Asp Pro Glu Leu Thr Asp Asp Tyr Leu
930                 935                 940                 945 aaa ctt ctg ctc caa caa gtt cgc cag agg ata cag tcg gca tct caa    3178
Lys Leu Leu Leu Gln Gln Val Arg Gln Arg Ile Gln Ser Ala Ser Gln
                950                 955                 960 tcc ggg aac cag tct tga gtttatattt tataagttga aaatggacag           3226
Ser Gly Asn Gln Ser *
            965 aacccagtgt ttggtttggt ggtcatgatt aggcgcctcc gtggatgtac atgtgccgtg   3286 ttctctaatt ttggcctcag agatgatgtt tacaccaccc actgcacttg ctttaaatgt   3346 tttacagatt ttgttagtgg tacatagcta tcatcaagag ctttagattt cgtgg        3401
```

<210> SEQ ID NO 2
<211> LENGTH: 966
<212> TYPE: PRT
<213> ORGANISM: Oryza sativa

<400> SEQUENCE: 2

Met Ser Glu Asp Ala Ser Val Gly Ala Ser Ser Thr Val Lys Ala
1               5                   10                  15

Gly Asp Asp Pro Glu Ala Thr Ile Glu Ile Asn Ile Lys Thr Leu Asp
            20                  25                  30

Ser Gln Val His Lys Leu Arg Val Lys Lys Asn Val Pro Val Leu Val
        35                  40                  45

Leu Lys Glu Lys Ile Val Glu Ala Thr Gly Val Pro Val Asp Gln Gln
    50                  55                  60

Arg Leu Ile Phe Arg Gly Arg Val Leu Lys Asp His Leu Leu Ser
65                  70                  75                  80

Glu Tyr His Leu Glu Asp Gly Tyr Thr Leu His Leu Val Ala Arg Arg
                85                  90                  95

Ala Ala Ala Glu Gly Gln His Ser Ser Gly Thr Ser Asp Glu Asn Thr

-continued

```
               100                 105                 110
His Ala Asn Val Asn Val Ala Gly Asn Gly Leu Leu Gly Asp Ile Ser
            115                 120                 125
Arg Ser Val Arg Asp Ile Leu Gly Ser Leu Gly Leu Ala Thr Pro Gly
        130                 135                 140
Gly Met Thr Asn Thr Thr Phe Ser Val Pro Leu Thr Thr Ala Pro Lys
145                 150                 155                 160
Gly Ala Asn Asn Val Asn Gly Arg Thr Gln Pro Gly Asn His Ala Gln
                165                 170                 175
Pro Gly Phe Ser Ile Leu Asn His Gln Ile Gln Val Ser Gln Leu Gln
            180                 185                 190
Pro Ala Gly Ser Ile Pro Arg Asn Met Val Ile Pro Asp Ser Leu Thr
        195                 200                 205
Thr Leu Leu Glu Tyr Ile Asn Arg Met Asp Gln Val Leu Gln Asn Asn
210                 215                 220
Gly Thr Pro Ser Val Asp Thr Asn Thr Gln Gln Pro Pro Arg Ser Asp
225                 230                 235                 240
Asp Ala Tyr Leu Asn Gln Arg Phe Pro Ser Pro Glu Val Leu Val Ser
                245                 250                 255
Val Ile Glu Arg Ala Gln Gln Leu Leu Gly Gly Ser Ala Ala Ser Ala
            260                 265                 270
Leu Ser His Leu Ala Gln Pro Ile Gln Arg Asp Ser Gly Thr Ser Asp
        275                 280                 285
Ala Ser Ile Arg Ser Gln Ile Gln Asn Glu Ser Ala Gln Leu Gly Val
        290                 295                 300
Ala Met Gln His Leu Gly Ala Met Phe Leu Glu Leu Gly Arg Thr Met
305                 310                 315                 320
Met Met Leu Arg Met Gly Pro Ser Pro Ala Asp Ala Phe Val Asn Ala
                325                 330                 335
Gly Ser Ser Val Tyr Ile Asn Ser Ala Gly Pro Asn Pro Ile Met Val
            340                 345                 350
Gln Pro Ser Phe Gln Asn Thr Pro Pro Phe Gly Val Ser Ser Ile Pro
        355                 360                 365
Val Leu Gly Gly Ile Ser Gly Ala Phe Gly Ile Val Asp Pro Ser Arg
    370                 375                 380
Thr Ser Ala Val Asn Thr His Gly Thr Ser Thr Ser Gly Ser Ser
385                 390                 395                 400
Ala Gly Met Thr Thr Ala Ser Ala Gly Ala Val Asn Glu Gly Arg Gln
                405                 410                 415
Asn Val Glu Arg Thr Gln Gly Gly Asn Pro Ser Ala Thr Ser Met His
            420                 425                 430
Gly Leu Pro Ala Arg Thr Val Ile Ala Ala Ile Pro Ala Arg Ser Thr
        435                 440                 445
Ala Glu Ala Pro Asn His Val Leu Ser Val Ile Leu Pro Val Gln Val
    450                 455                 460
Arg Ser Gln Val Ala Met Pro Asn Gln Ser Thr Val Ser Gln Gly Ser
465                 470                 475                 480
Gln Thr Ala Val Gly Gly Ser Gln Pro Gln Ala Ser Val Gly Gly
                485                 490                 495
Val Ala Ser Ile Pro Ser Ile Val Ala Gln Val Thr Ala Gln Val Ala
            500                 505                 510
Asn Ala Leu Ser Ala Asn Gln Gln Gly Gln Val Ser Ser Ser Ala Gln
        515                 520                 525
```

-continued

```
Asn Thr Val Asp Gln Gly Ser Arg Ser Val Thr Thr Asn Gly Val Asp
    530                 535                 540
Asn Val Asp Ser Leu Val Ser Ala Ser Thr Gln Leu Gln Asn Glu Leu
545                 550                 555                 560
Ser Asp Ser Asn Asn Gly Arg Thr Ser Leu Asn Ala Gln Ser Leu Val
                565                 570                 575
Ala Gly Ala Gly Ile Ser Pro Ser Asn Thr Ser Asp Pro Asn Leu Ala
            580                 585                 590
Ser Glu Asp Ser Ser Thr Glu Asn Ala Pro Asn Ile Gly Ser Ile Gln
        595                 600                 605
Gln His Pro Glu Met Glu Gly Ile His Ala Asp Asn Val Arg Lys Pro
    610                 615                 620
Ser Glu Glu Ser Thr Thr Ala Asn Leu Val Gly Gln Ile Thr Thr Thr
625                 630                 635                 640
Cys Thr Asp Asp Ile Ser Val Asn Arg Ser Ala Glu Asn Ser Ser Gln
                645                 650                 655
Lys Asn Ile Pro Leu Asp Gly Val Ser Ala Gln Ser Ile Lys Pro Ser
            660                 665                 670
Ala Ser Ser Arg Ser Glu Pro Val Gly Leu Gly Gly Leu Gln Pro
        675                 680                 685
Lys Arg Arg Ser Arg Thr Ala Lys Pro Pro Gly Ser Ser Ser Asp Thr
    690                 695                 700
Gly Glu Val Val Asn Ser Ser Arg Ile Ser Asn Ser Gln Asn Ala Val
705                 710                 715                 720
Ser Met Gly Gln Gln Val Leu Gln Ala Leu Ala Ser Gln Asn Thr Asn
                725                 730                 735
Val Asn Arg Ser His Val Thr Asp Ser Pro Leu Pro Ser Thr Thr Ser
            740                 745                 750
Gln Phe Ser Gly Gly Met Pro Pro Arg Arg Gln Gly Gly Glu Gly Gln
        755                 760                 765
Val Asp Phe Gly Ser Met Ile Ser Ser Val Leu Asn Asn Pro Ala Phe
    770                 775                 780
Gly Asn Leu Leu Ser Asn Val Ala Glu Gln Thr Gly Met Gly Ser Ala
785                 790                 795                 800
Gly Asp Leu Arg Asn Met Val Glu Glu Cys Ala Gln Ser Pro Ala Ile
                805                 810                 815
Met Asp Thr Met Ser Asn Leu Val Gln Asn Val Asp Gly Ser Gly Arg
            820                 825                 830
Gly Gln Gly Gly Ile Asp Leu Ser Arg Met Met Gln Met Met Pro
        835                 840                 845
Val Val Ser Gln Val Leu Gly Gly Ala Gly Ala Arg Pro Ala Gly Thr
    850                 855                 860
Asn Ser Gly Gln Ser Arg Leu Gln Pro Arg Arg Ser Asp Met Arg Val
865                 870                 875                 880
Asp Asp Ala Ser Asp Tyr Gly Asn Ser Gln Ile Asp Leu His Gln Ala
                885                 890                 895
Arg Glu His Ile Glu Gln His Asp Ser Pro Arg Asp Ile Phe Gly Ala
            900                 905                 910
Val Leu Glu Thr Ala Ala Gln Ala Tyr Gly Glu Asp Glu Ser Ile Glu
        915                 920                 925
Asp Met Leu Glu Glu Leu Val Ser Asp Pro Glu Leu Thr Asp Asp Tyr
    930                 935                 940
```

```
-continued

Leu Lys Leu Leu Leu Gln Gln Val Arg Gln Arg Ile Gln Ser Ala Ser
945                 950             955                 960

Gln Ser Gly Asn Gln Ser
            965
```